(12) United States Patent
Tu et al.

(10) Patent No.: US 6,231,570 B1
(45) Date of Patent: *May 15, 2001

(54) ELECTRODE CATHETER SYSTEM FOR TISSUE ABLATION

(76) Inventors: Hosheng Tu, 2151 Palermo; Cary Hata, 2500 San Simon St., both of Tustin, CA (US) 92782

( * ) Notice: Subject to any disclaimer, the term of this patent is extended or adjusted under 35 U.S.C. 154(b) by 0 days.

This patent is subject to a terminal disclaimer.

(21) Appl. No.: 09/094,953

(22) Filed: Jun. 15, 1998

Related U.S. Application Data (63) Continuation of application No. 08/856,726, filed on May 15, 1997, now Pat. No. 5,792,140.

(51) Int. Cl.$^7$ .................................................. A61B 18/18
(52) U.S. Cl. .............................. 606/41; 606/50; 607/122
(58) Field of Search ....................... 606/41, 42, 48–50; 607/101, 122, 100, 102–105, 113

(56) References Cited

U.S. PATENT DOCUMENTS 5,370,675 * 12/1994 Edwards et al. ..................... 607/101
5,800,484 * 9/1998 Gough et al. ......................... 607/104

* cited by examiner

*Primary Examiner*—John P. Leubecker
*Assistant Examiner*—Roy Gibson (57) ABSTRACT

An improved ablation catheter possessing a plurality of inner micro-catheters, each micro-catheters including at least one multiple-needle electrode is used in ablating a large arrhythmogenic region instead of an arrhythmogenic point of a patient. This catheter is particularly useful for treating the patient with atrial fibrillation (AFib) indications. A catheter including a delivery catheter and a plurality of inner micro-catheters with each one having at least one multiple-needle electrode is inserted into the chambers of the heart to create a plurality of deep, large, and linear lesions by applying radiofrequency energy and cooled fluid to said electrode.

4 Claims, 8 Drawing Sheets

ELECTRODE CATHETER SYSTEM FOR TISSUE ABLATION

CROSS-REFERENCE TO RELATED APPLICATIONS

This application is a application of U.S. application Ser. No. 08/856,726, entitled "Catheter Having Cooled Multiple-Needle Electrode" filed May 15, 1997, now U.S. Pat. No. 5,792,140 and is incorporated herein by reference.

FIELD OF THE INVENTION

The present invention generally relates to improved constructions for a cardiovascular catheter. More particularly, this invention relates to a delivery catheter containing multiple retractable micro-catheters and methods for ablating tissues via the micro-catheters, wherein each micro-catheter has one cooled multiple-needle electrode and has irrigation capabilities for ablating tissues resulting in a plurality of deeper and linear lesions.

BACKGROUND OF THE INVENTION

Symptoms of abnormal heart rhythms are generally referred to as cardiac arrhythmias, with an abnormally rapid rhythm being referred to as a tachycardia The present invention is concerned with the treatment of tachycardias which are frequently caused by the presence of an "arrhythmogenic site" or "accessory atrioventricular pathway" close to the inner surface of the chambers of a heart. The heart includes a number of normal pathways which are responsible for the propagation of electrical signals from the upper to lower chambers necessary for performing normal systole and diastole function. The presence of arrhythmogenic site or accessory pathway can bypass or short circuit the normal pathways, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia It is important for a physician to accurately steer the catheter to the exact site for ablation. Once at the site, it is important for a physician to control the emission of energy to ablate the tissue within the heart Of particular interest to the present invention are radiofrequency (RF) ablation protocols which have been proven to be highly effective in tachycardia treatment while exposing a patient to minimal side effects and risks. Radiofrequency catheter ablation is generally performed after conducting an initial mapping study where the locations of the arrhythmogenic site and/or accessory pathway are determined. After a mapping study, an ablation catheter is usually introduced to the target heart chamber and is manipulated so that the ablation tip electrode lies exactly at the target tissue site. Radiofrequency energy or other suitable energy is then applied through the tip electrode to the cardiac tissues in order to ablate the tissue of arrhythmogenic site or the accessory pathway. By successfully destroying that tissue, the abnormal signal patterns responsible for the tachycardia may be eliminated. However, in the case of atrial fibrillation (AFib), multiple arrhythmogenic sites and/or multiple accessory pathways exist. The conventional catheter with a single ablation tip electrode can not effectively cure the symptoms.

Atrial fibrillation is believed to be the result of the simultaneous occurrence of multiple wavelets of functional re-entry of electrical impulses within the atria, resulting in a condition in which the transmission of electrical activity becomes so disorganized that the atria contracts irregularly. Once considered a benign disorder, AFib now is widely recognized as the cause of significant morbidity and mortality. The most dangerous outcome from AFib is thromboembolism and stroke risk, the latter due to the chaotic contractions of the atria causing blood to pool. This in turn can lead to clot formation and the potential for an embolic stroke. According to data from the American Heart Association, about 75,000 strokes per year are AFib-related.

A catheter utilized in the endocardial RF ablation is inserted into a major vein or artery, usually in the neck or groin area For epicardial ablation, a catheter is percutaneously introduced into the chest cavity through a small surgery hole, followed by penetrating through a punctured hole through the pericardium into the epicardial cavity.

The tip section of a catheter is referred to here as the portion of that catheter shaft containing the electrode or electrodes which may be deflectable. In one embodiment, the catheter is then guided into the appropriate chamber of the heart by appropriate manipulation through the vein or artery. The tip section of a conventional electrophysiology catheter that is deflectable usually contains one large electrode about 4 mm in length for ablation purpose. The lesion is generally not deep because of short energy delivery period due to potential impedance increase at the ablation site. And the lesion is not long to form a linear lesion.

Imran in U.S. Pat. No. 5,281,218 teaches a needle electrode attached on a catheter for radiofrequency ablation. In a co-pending application U.S. Ser. No. 08/856,726, filed May 15, 1997, Tu et al. describes a catheter having at least one multiple-needle electrode to enhance the RF energy delivery to make a deeper and larger lesion. However in the case of atrial fibrillation, it is frequently necessary to create several linear lesions. Therefore there is a need for a new and improved catheter system having a plurality of retractable micro-catheters, with each one having cooled multiple-needle electrodes for making deep and large multiple lesions in the myocardium or epicardium of the heart

SUMMARY OF THE INVENTION

In general, it is an object of the present invention to provide a delivery catheter containing multiple retractable ablation micro-catheters. It is another object of the present invention to provide an ablation catheter system having a delivery catheter comprising a plurality of retractable microcatheters, each with at least one cooled multiple-needle electrode which can be used in ablating the arrhythmogenic region instead of an arrhythmogenic point of a patient. This catheter is particularly useful for treating a patient with atrial fibrillation (AFib) indications.

In one embodiment, an ablation catheter system comprises a delivery catheter having a distal section, a distal end, a proximal end, and at least one lumen extending therebetween. A handle is attached to the proximal end of the delivery catheter. A plurality of retractable inner micro-catheters is located within the lumen of the delivery catheter, each micro-catheter having a distal tip section, a distal end, a proximal end, and a central lumen extending therebetween, wherein the distal tip section has at least one pre-shaped L-shape electrode. A deployment means for deploying the plurality of the retractable inner micro-catheters out of the delivery catheter is located at the handle and is connected to each of the retractable inner micro-catheters.

In another embodiment, the multiple-needle electrode is the tip electrode. In an alternate embodiment, the multiple-needle electrode contains a plurality of needles on said electrode. In a further embodiment, at least one needle on the at least one electrode of each inner-catheters faces outwardly toward the tissue surface to be ablated in endocardial ablation procedures or faces inward toward the epicardial tissue surface in epicardial ablation procedures. Therefore, at ablation time, the needles are positioned essentially perpendicular to the tissues to be ablated. In still another embodiment, the needles face at different directions so as to contact the endocardial tissue when a bi-directional deflectable catheter is used in the ablation procedures. The retractable inner micro-catheters are at a non-deployed state when it is positioned inside the delivery catheter. This non-deployed state is maintained during the catheter insertion operation into a patient and during withdrawal of the catheter from a patient.

The retractable inner micro-catheters are at a deployed state when they are advanced out of the distal end of said delivery catheter. Deployment of the inner micro-catheters is accomplished by a pushing action on the push-pull deployment mechanism at the handle. In one particular embodiment, the tip section of each deployed micro-catheter has a preformed shape so that the electrode of the multiple-needle electrodes would extend outwardly and radially of the delivery catheter when deployed. In a preferred embodiment, the distal tip section of the plurality of micro-catheters has a preformed L-shape so that when the micro-catheters contact a tissue surface, a linear contact line between a micro-catheter and the tissue is formed for linear ablation. The degree of deployment is controlled by the pushing action at the push-pull mechanism on the handle and is proportional to the push distance on the push-pull plunger of the push-pull mechanism which is quantifiable and controllable.

In another embodiment, each deployed inner micro-catheter has at least one multiple-needle electrode, wherein the needle has a flat top with a circular ring and an outlet port at its flat top. The flat top is provided with at least one drainage trough at its flat top for fluid to discharge from the side of the flat top. The flat-top circular ring of the needles of each electrode may be positioned at the forward side facing the target tissue. After finishing the ablation operation, the retraction of the micro-catheters is accomplished by pulling back axially the inner micro-catheter relative to the delivery catheter. The degree of retraction is mainly controlled by the pulling action at the push-pull mechanism on the handle.

A fluid conveying lumen is associated with the elongate catheter shaft, and preferably is disposed within the lumen of the inner micro-catheters along the longitudinal axis thereof. The lumen is adapted to communicate with a fluid supply source to convey fluid from the source and through the lumen to be discharged through an outlet port disposed at the distal tip of the hollow needles of the electrodes.

The invention also comprises a method and system for controlling the flow rate of fluid through the lumen to optimize the cooling of the energy delivering electrode of the catheter. The control system preferably regulates the flow rate based on signals representative of the temperature of the catheter tip and/or tissue impedance.

In one embodiment, at least a conducting wire which is soldered to the electrode passes through the lumen of each inner micro-catheter and the interior void of the handle and is thereafter soldered to a contact pin of the connector secured at the proximal end of the handle. Therefrom, the conducting wire is connected to an external RF generator for ablation operations and/or to an EKG monitor for recording and displaying of the endocardial or epicardial electrical signal. In an alternate embodiment, the micro-catheter is made of a conductive material and the micro-catheter itself serves as the conducting means for RF energy transmission and EKG signal transmission.

In one embodiment, the catheter system further comprises a temperature sensing and close-loop temperature control mechanism for the electrode having at least one temperature sensor at the tissue contact site of the electrodes. The location of the temperature sensor is preferably in the proximity of one of the needles of the electrodes.

In a particular embodiment, the length of the multiple-needle electrode is 4 mm or longer. In an alternate embodiment, the needles on an electrode are equally spaced and the distance between the needle tip is 4 mm or less. The height of the needle is usually 1 mm or less. The material for the multiple-needle electrodes may consist of conductive metals such as platinum, iridium, gold, silver, stainless steel, Nitinol, or an alloy of their mixtures.

In a still further embodiment, the tip section of the inner micro-catheter comprising the electrodes is formed of a conducting material without catheter shaft. The multiple-needle electrode in this embodiment is formed of a flexible metal mesh or metal coil that can be retracted into the delivery catheter during inserting and withdrawal of said catheter system in an electrophysiology procedure.

In order to provide increased torsional rigidity to the catheter shaft of the delivery catheter, the shaft material preferably comprises a polymeric tube having a Durometer in the range from 30D to 90D, usually from 40D to 65D. Preferably, the shaft has a composite structure including a base layer of a relatively low Durometer material, a stiffening layer, for example, metal braid or coil, and an outer layer comprising the biocompatible polymeric material or the material that may render itself biocompatible by surface treatment. To enhance biocompatibility, the catheter shaft further comprises surface coating of heparin on the surface of the catheter shaft. It is hypothesized that the coated heparin forms a barrier, while not releasing heparin from said surface, between the blood and the catheter surface to enhance biocompatibility during electrophysiology procedures. In a further embodiment, an ablation catheter further comprises construction of low surface energy substrates or surface treatment of low surface energy substrates, such as Teflon( type fluorinated polymers, to mitigate blood coagulation during high energy ablation. Fluorinated polymer can be the construction material for the catheter system or deposited on the shaft surface via plasma coating technology or the like.

A method for operating a steerable ablation catheter system having at least one multiple-needle electrode at the tip section of a plurality of deployable inner micro-catheters within a heart chamber comprises percutaneously introducing the delivery catheter through a blood vessel to the heart chamber, wherein the multiple-needle electrode is deployed by advancing the retractable inner micro-catheters forward and forming the desired electrode pre-shape; deflecting the distal section of the inner catheters about a transverse axis to position the multiple-needle electrode near a target region on an interior wall of the heart chamber; intimately contacting the electrode, including the needles, with the intracardiac tissue; and applying radiofrequency energy to the target location through the needles of this invention.

The method and catheter of the present invention have several significant advantages over known catheter or ablation techniques. In particular, the cooled multiple-needle electrode of a plurality of micro-catheters of this invention may result in a plurality of deeper, larger and linear lesions which is highly desirable in the AFib treatment

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
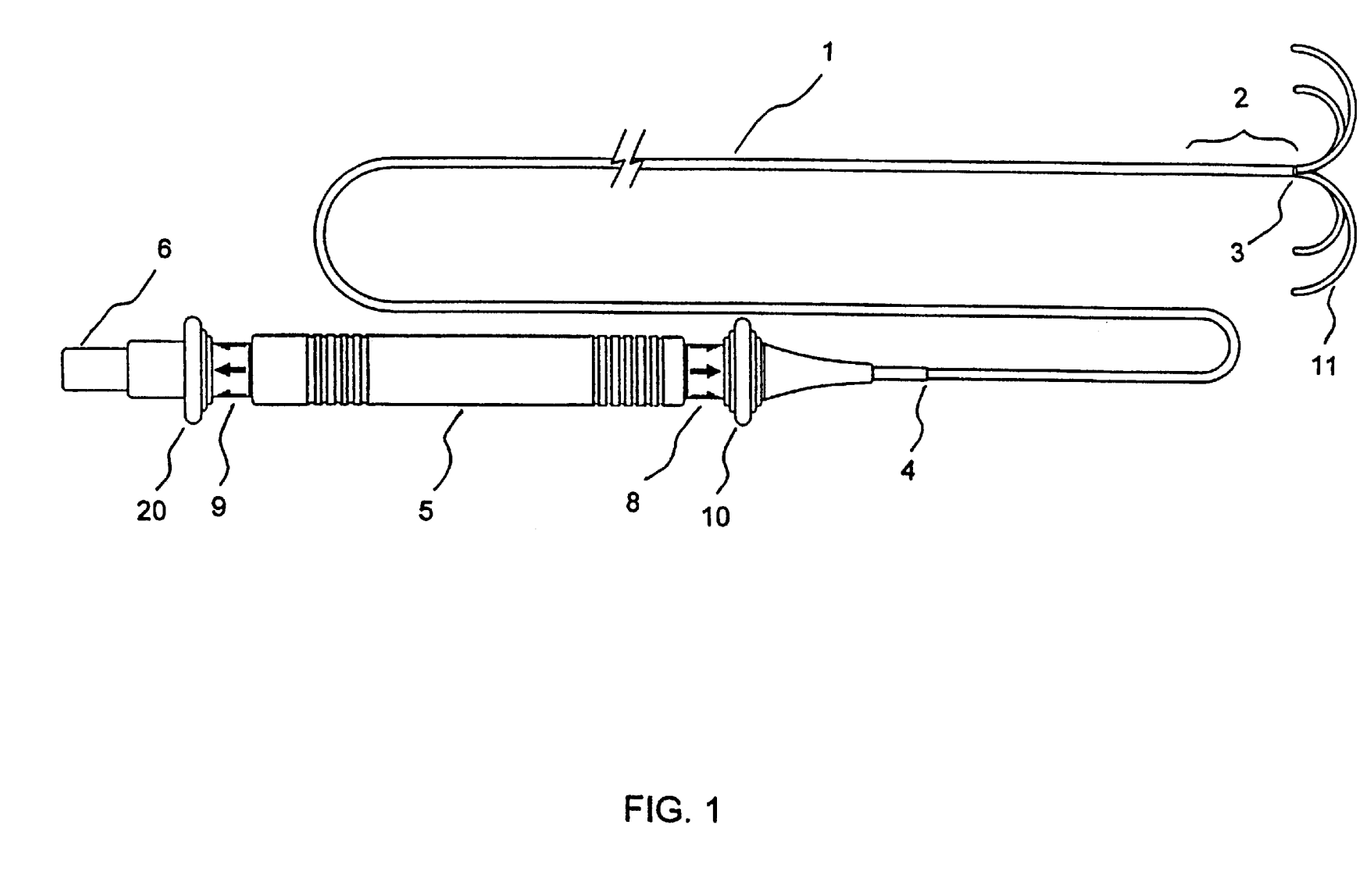
FIG. 1 is an overall view of a catheter system comprising a delivery catheter and a plurality of retractable micro-catheters constructed in accordance with the principles of the present invention.

FIG. 1 shows an overall view of a catheter system comprising a delivery catheter and a plurality of retractable micro-catheters constructed in accordance with the principles of the present invention. The catheter system comprises a delivery catheter 1 having a distal section 2, a distal end 3, a proximal end 4, and at least one lumen extending therebetween. A handle 5 is attached to the proximal end 4 of the delivery catheter 1. A plurality of retractable inner micro-catheters 11 is located within the lumen 7 of the delivery catheter 1, each micro-catheter 11 having a distal tip section 12, a distal end 13, a proximal end 14, and a central lumen 17 extending therebetween, wherein the distal tip section 12 has at least one electrode means 15.

The connector 6 secured at the proximal end of the catheter system is part of the handle section 5. The handle 5 has one steering mechanism 8 and one micro-catheters deployment mechanism 9. The steering mechanism 8 is to deflect the tip section of the delivery catheter 1. In one embodiment, by pushing the front plunger 10 of the handle 5, the tip section 2 of the delivery catheter 1 deflects to one direction. By pulling the front plunger 10, the tip section returns to its neutral position. In another embodiment, the steering mechanism 8 at the handle 5 comprises means for providing a plurality of deflectable curves on the distal tip section of the delivery catheter 1.

The deployment mechanism 9 comprises a push-pull ring or a plunger 20 for deploying the retractable inner micro-catheters 11. The tip section of the inner micro-catheters 11 is advanced outwardly of the delivery catheter 1 during catheter deployment phase for ablation purposes. While the catheter is introduced into the body or removed from the body of a patient, all the tip sections 12 of the inner micro-catheters 11 are retracted into the delivery catheter 1 by pulling back the rear plunger 20.

Figure 2:
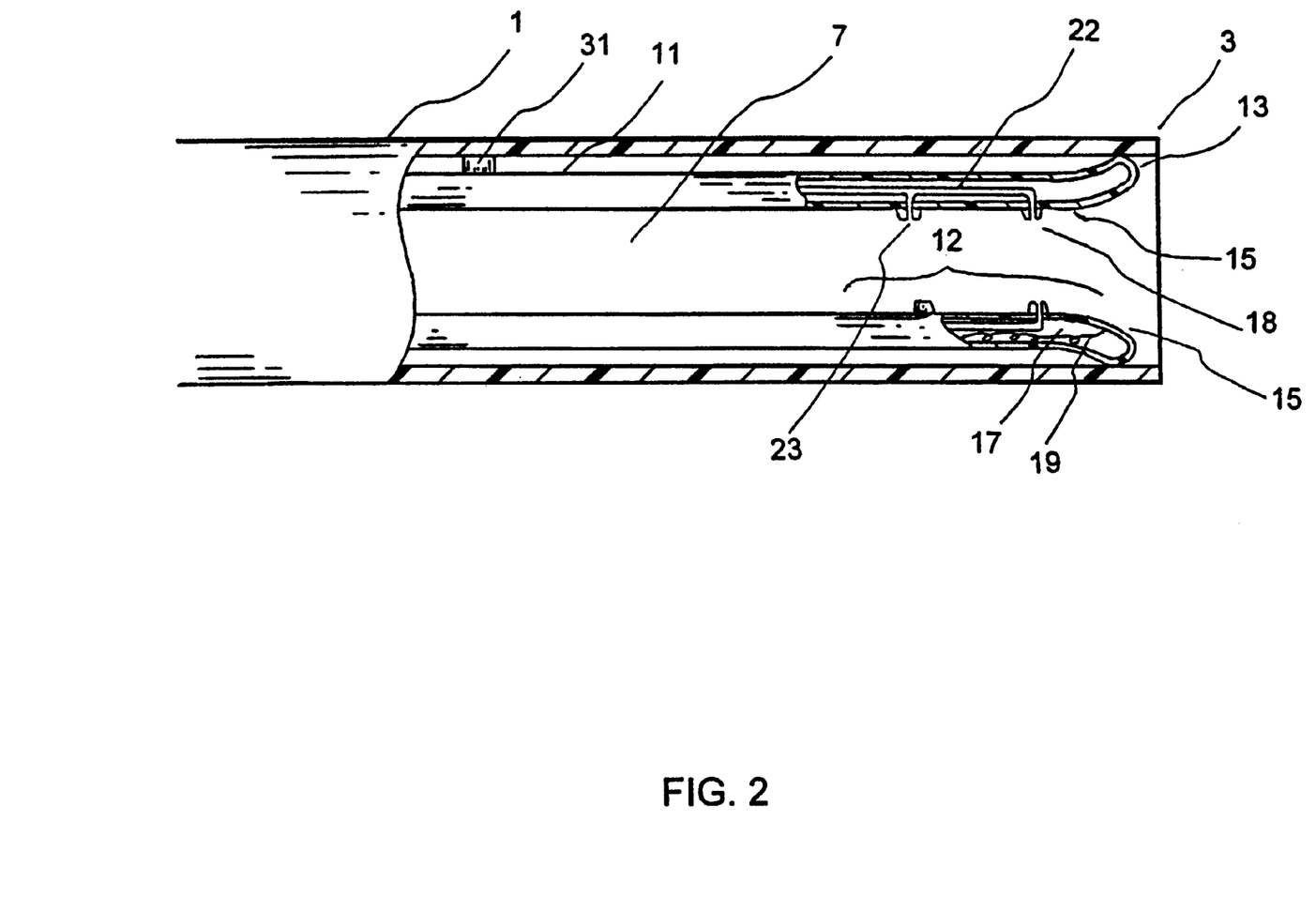
FIG. 2 is a cross-sectional view of the distal portion of the catheter system at non-deployed state.

FIG. 2 shows a cross-sectional view of the distal portion 2 of the delivery catheter 1 at non-deployed state of FIG. 1. The tip section of each inner micro-catheter 11 comprises at least one electrode means 15 which has a plurality of flat-top needles 18. The electrodes are formed of conducting material. In one embodiment, at least one electrode is a metal mesh 35 or a metal coil 36 securely wrapped outside of a catheter shaft of the inner micro-catheter 11, wherein the electrode has a plurality of needles 18. To prevent blood from backflow into the delivery catheter 1, a silicone type sealer 31 is optionally installed at certain opening of the delivery catheter 1 between the delivery catheter 1 and the inner micro-catheters 1.

Figure 3:
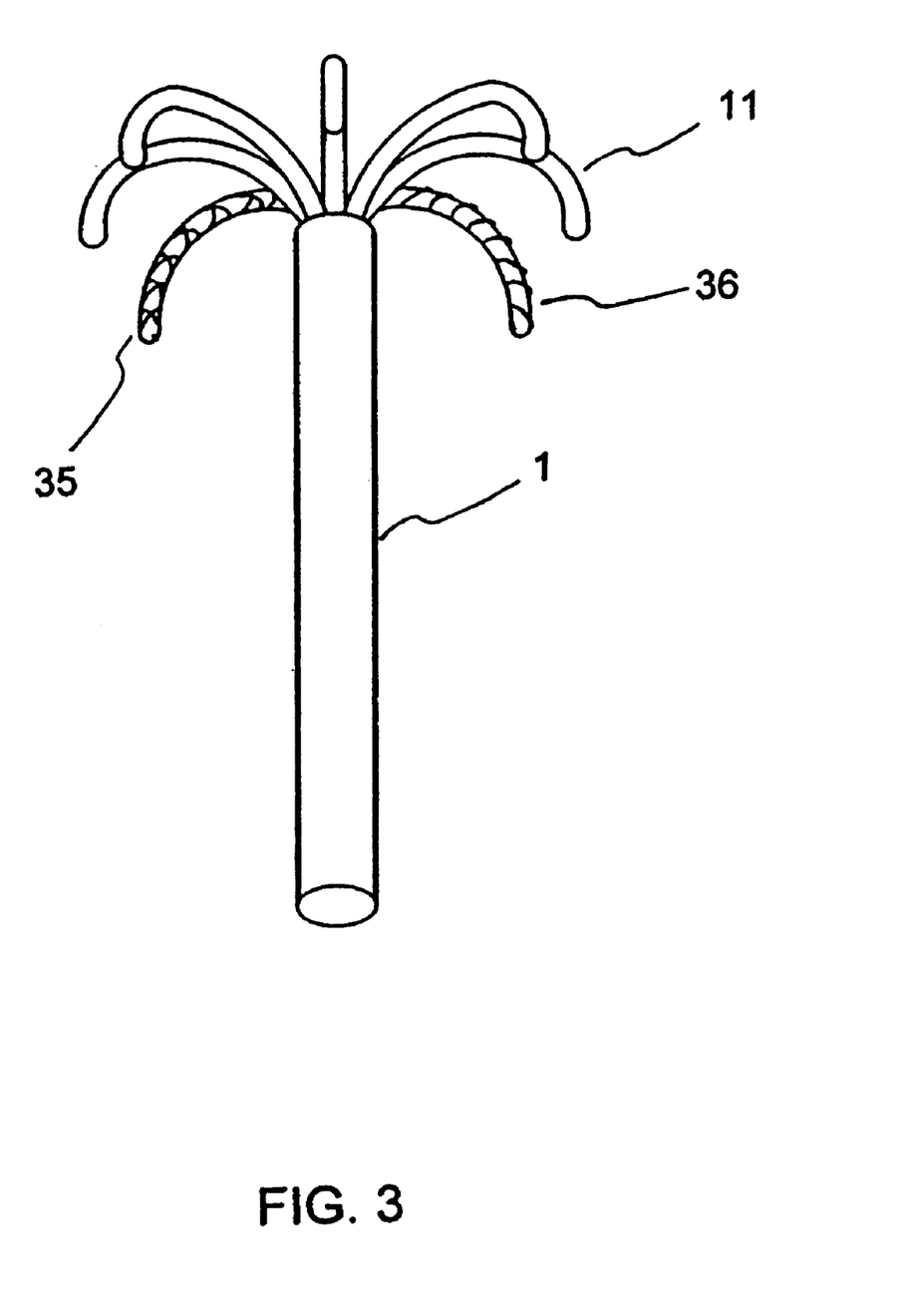
FIG. 3 is a close-up view of the distal tip portion of the catheter system at deployed state.

FIG. 3 shows a close-up view of the distal tip portion of the catheter system at deployed state. A plurality of micro-catheters 11 has a pre-formed shape and extends outwardly and radially so that the outer surface of all the micro-catheters would contact a plane, which is perpendicular to the axis of the delivery catheter 1.

Figure 4:
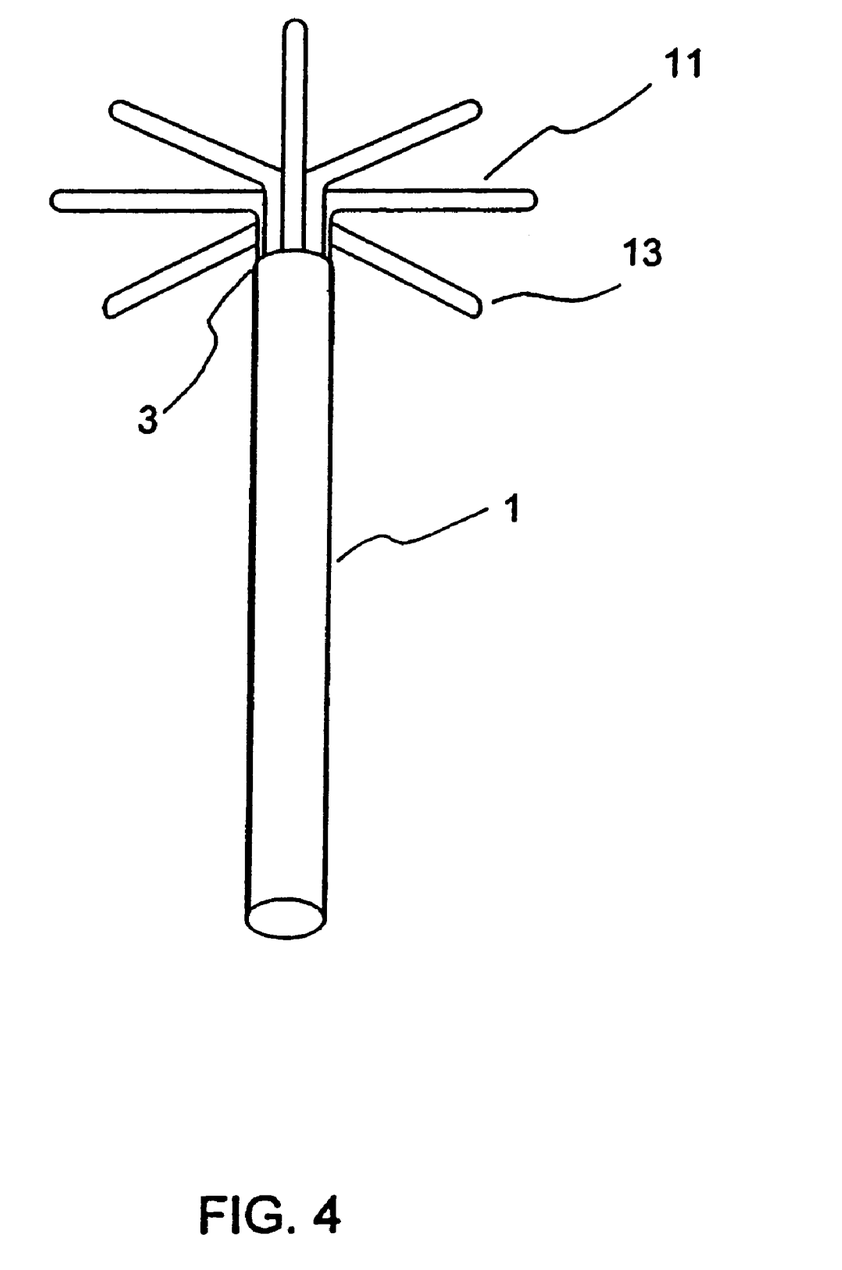
FIG. 4 is a close-up view of the distal tip portion of an alternate catheter system having preformed L-shape micro-catheters at deployed state.
Figure 5A:
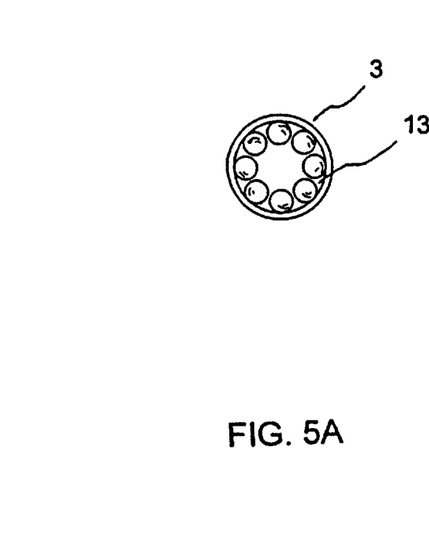
FIG. 5A is a transverse view of the distal end of an alternate catheter system having preformed L-shape micro-catheters at non-deployed state.
Figure 5B:
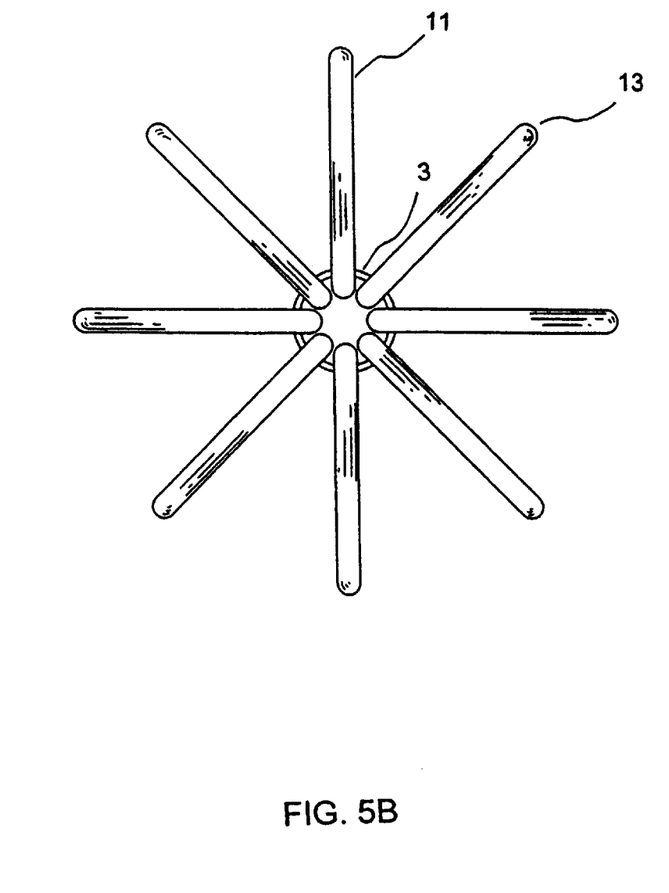
FIG. 5B is a transverse view of the distal end of an alternate catheter system having preformed L-shape micro-catheters at deployed state.

FIG. 4 shows a close-up view of the distal tip portion of an alternate catheter system at deployed state. A plurality of micro-catheters 11A has a pre-formed L-shape and extends outwardly and radially so that the outer surface of all the micro-catheters would contact a plane, which is perpendicular to the axis of the delivery catheter 1. In this case, the contact between a micro-catheter and the perpendicular plane forms a linear line. This is further illustrated in FIGS. 5A and 5B. FIG. 5A shows a transverse view of the tip 3 of the delivery catheter 1. The tip 13 of the micro-catheters 11 is located within the tip section 2 of the delivery catheter under non-deployed state. FIG. 5B shows a transverse view of the tip 3 of the delivery catheter and the distal tip sections 12 of the micro-catheters 11 under deployed state. This linear type ablation is particularly effective in treating cancers, tumors or other tissue blocks. By slightly rotating the catheter system from the handle 5, the ablation operations can continue to cover a large circular area of the tissues.

Figure 6:
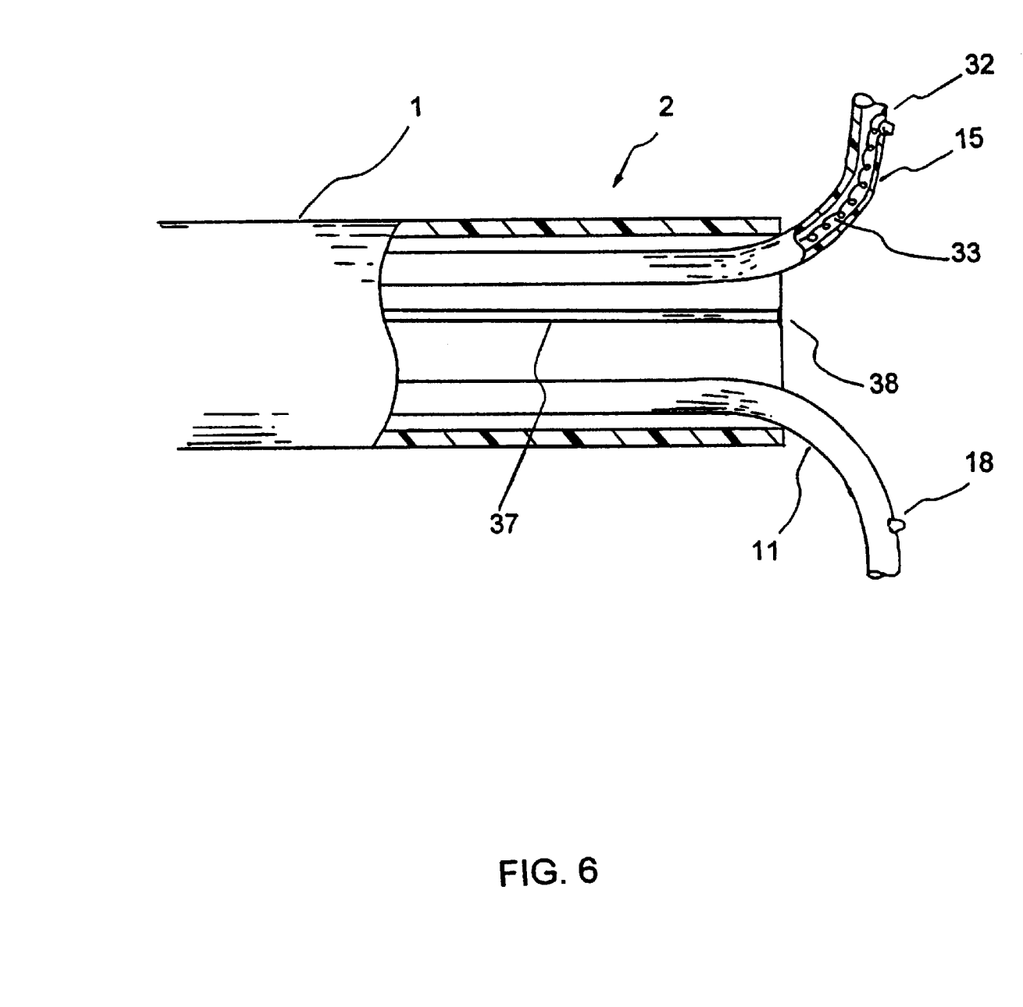
FIG. 6 is a cross-sectional view of the distal portion of the catheter system at deployed state.

FIG. 6 shows a cross-sectional view of the tip section 2 of the delivery catheter under deployed state. One of the micro-catheters 11 has at least one temperature sensor 32. The multiple-needle electrode means 15 has an insulated conducting wire 19 secured to the electrode means 15 that passes through the lumen 17 of each inner micro-catheter 11 and is soldered to a contact pin of the connector 6 at the proximal end of the handle 5.

The conducting wire 19 from the connector end is externally connected to an external EKG monitor for signal display or to an RF generator for RF energy delivery. Therefrom, the RF energy is transmitted through the conducting wire to the multiple-needle electrode and energy delivered to the target tissue. In an alternate embodiment, the micro-catheter 11 is made of a conducting material and serves as the conductor.

The ablation catheter further comprises a steering mechanism 8 at the handle 5 for controlling the deflection of the distal section 2 of the delivery catheter 1. Usually a rotating ring or a push-pull plunger 10 is employed in the steering mechanism. In another embodiment, the steerable delivery catheter comprises a bi-directional deflection or multiple curves deflection of the tip section having at least one multiple-needle electrode. One end of the steering wire 37 is attached at certain point 38 of the tip section 2 of the delivery catheter 1. The other end is attached to the steering mechanism 8 at the handle. The steering mechanism on a steerable catheter or device is well known to those who are skilled in the art.

A temperature sensor 32, either a thermocouple means or a thermister means, is constructed at the proximity of one needle 18 of the electrode means 15 to measure the tissue contact temperature when RF energy is delivered. The temperature sensing wire 33 from the thermocouple or thermister is connected to one of the contact pins (not shown) of the connector 6 and externally connected to a transducer and to a temperature controller. The temperature reading is thereafter relayed to a close-loop control mechanism to adjust the RF energy output. The RF energy delivered is thus controlled by the temperature sensor reading or by a pre-programmed control mechanism.

Each tip section of the micro-catheters 11 having at least one multiple-needle electrode formed of conducting material can be deployed out of the delivery catheter 1 and retracted into said delivery catheter 1 by a deployment mechanism 9 at the handle 5.

Figure 7:
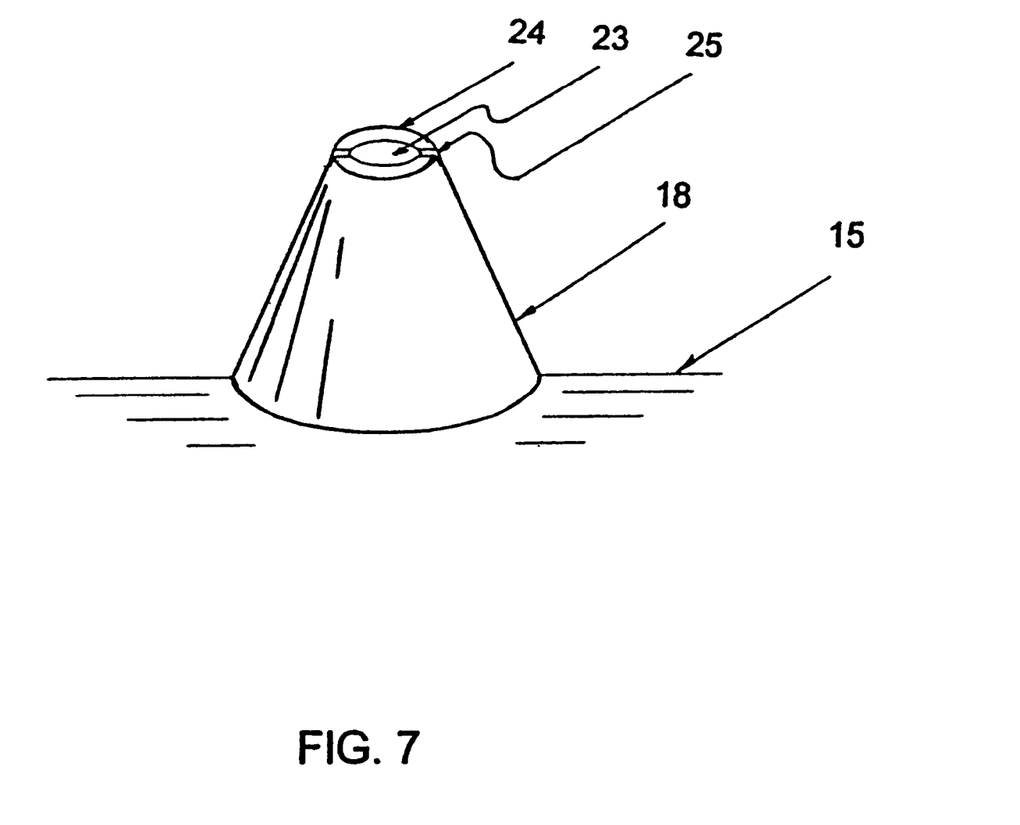
FIG. 7 is a perspective view of the flat-top needle of an electrode of the inner micro-catheter tip section of FIG. 2.

A plurality of needles 18 on the at least one electrode means 15 has a needle structure comprising a hollow passage 22 with an outlet port 23 (as shown in FIG. 7), and means formed within the needle structure for providing fluid communication and commensurate flow of fluid originating inside the needle structure 18 of the micro-catheters 11 to portions of the electrode exterior surface through a plurality of passages 22 and outlet ports 23 which direct the fluid flow from inside the inner micro-catheter shaft over the exterior surface of the needles to provide a fluid protective layer surrounding the electrode to minimize temperature elevation of the electrode when contacted with biological tissues.

FIG. 7 shows a perspective view of the needles of the multiple-needle electrode of the inner catheter, wherein the needle comprises a flat top 24, and at least one drainage trough 25 at its flat top. In one embodiment, a plurality of needles 18 on the at least one electrode means 15, which form a multiple-needle electrode, wherein each needle 18 has a needle structure comprising a hollow passage with an outlet port; and a deployment means 9 for deploying the plurality of the retractable inner micro-catheters out of the delivery catheter, wherein the deployment means is located at the handle and is connected to each of the retractable inner micro-catheters.

Figure 8:
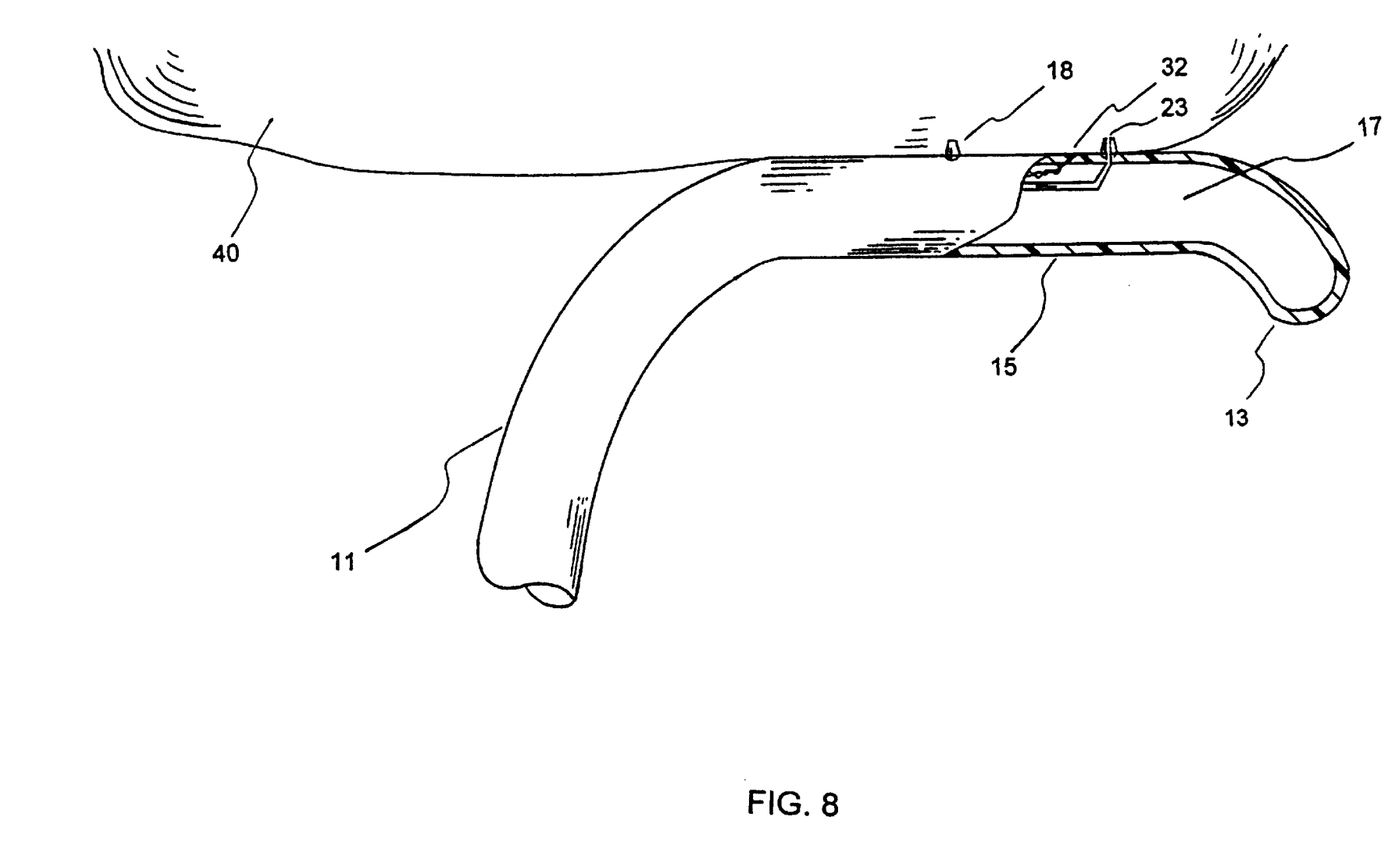
FIG. 8 shows contact of one of the micro-catheters of this invention with the tissue.

FIG. 8 shows the contact of the needles 18 of the cooled multiple-needle electrode means 15 of the inner micro-catheters 11 with the target tissue 40. The needles of the inner micro-catheters may contact the tissue at an angle essentially perpendicular to the target tissue 40. The RF energy is applied thereafter while a cooled fluid is provided either simultaneously or intermittently. A plurality of deep and linear lesions is created in a region for the treatment of a tachycardia.

From the foregoing, it should now be appreciated that an improved ablation catheter system comprising a plurality of micro-catheters with each one having multiple-needle electrode and a cooling fluid capability has been disclosed for ablation procedures, including endocardial, epicardial, or body tissue ablations. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. An ablation catheter system comprising:

a delivery catheter having a distal section, a distal end, a proximal end, and at least one lumen extending therebetween;

a handle attached to the proximal end of the delivery catheter;

a plurality of retractable inner micro-catheters located within the lumen of the delivery catheter, each micro-catheter having a distal tip section, a distal end, a proximal end, and a central lumen extending therebetween, wherein the distal tip section is pre-shaped as an L-shape and has at least one electrode means; and a deployment means for deploying the plurality of the retractable inner micro-catheters out of the delivery catheter, wherein the deployment means is located at the handle and is connected to each of the retractable inner micro-catheters.

2. A method for operating an ablation catheter system within a heart chamber, the ablation catheter system comprising a delivery catheter having a distal section, a distal end, a proximal end, and at least one lumen extending therebetween; a handle attached to the proximal end of the delivery catheter; a plurality of retractable inner micro-catheters located within the lumen of the delivery catheter, each micro-catheter having a distal tip section, a distal end, a proximal end, and a central lumen extending therebetween, wherein the distal tip section has at least one electrode means and is pre-shaped; a plurality of needles on the at least one electrode means which form a multiple-needle electrode, wherein each needle has a needle structure comprising a hollow passage with an outlet port; a deployment means for deploying the plurality of inner micro-catheters out of the delivery catheter, wherein the deployment means is located at the handle and is connected to each of the retractable inner micro-catheters; means formed within the needle structure for providing fluid communication and commensurate flow of fluid originating inside the needle structure to portions of the exterior surface of the at least one electrode through the said hollow passage which directs the fluid flow from inside the central lumen of the inner micro-catheters over the exterior surface of the needles to provide a fluid protective layer surrounding the electrode to minimize temperature elevation of the electrode when contacted with biological tissues; and RF energy generating means connected to the at least one needle electrode, wherein the RF energy is delivered to the needles of the multiple-needle electrode;

the method comprising:

(a) percutaneously introducing the delivery catheter through a blood vessel to the heart chamber; wherein the plurality of multiple-needle electrodes is deployed by advancing the retractable inner micro-catheters forward;

(b) deploying the multiple-needle electrodes of the micro-catheters out of the delivery catheter;

(c) intimately contacting the plurality of multiple-needle electrodes with the tissue;

(d) applying RF energy to the multiple-needle electrodes for ablation; and (e) cooling the electrodes by releasing cooled fluid through the outlet ports of the needles.

3. A method for operating an ablation catheter system as in claim 2, wherein the fluid is selected from the group consisting of saline, cooled saline, heparin, therapeutic fluid, anti-inflammatory fluid, and anti-cancer fluid.

4. An ablation catheter system comprising:

a delivery catheter having a distal section, a distal end, a proximal end, and at least one lumen extending therebetween;

a handle attached to the proximal end of the delivery catheter;

a plurality of retractable inner micro-catheters located within the lumen of the delivery catheter, each micro-catheter having a distal tip section, a distal end, a proximal end, and a central lumen extending therebetween, wherein the distal tip section has at least one pre-shaped L-shape electrode; and a deployment means for deploying the plurality of the retractable inner micro-catheters out of the delivery catheter, wherein the deployment means is located at the handle and is connected to each of the retractable inner micro-catheters.

* * * * *